United States Patent [19]

Senturia

[11] 4,209,796
[45] Jun. 24, 1980

[54] CHARGE-FLOW TRANSISTORS HAVING METALLIZATION PATTERNS

[75] Inventor: Stephen D. Senturia, Cambridge, Mass.

[73] Assignee: Massachusetts Institute of Technology, Cambridge, Mass.

[21] Appl. No.: 853,059

[22] Filed: Nov. 21, 1977

[51] Int. Cl.$^2$ .......................................... H01L 29/76
[52] U.S. Cl. ...................................... 357/23; 357/41; 357/25; 357/52
[58] Field of Search .................................... 357/23, 41

[56] References Cited
U.S. PATENT DOCUMENTS

| | | | |
|---|---|---|---|
| 4,044,373 | 8/1977 | Nomiya et al. | 357/41 |
| 4,062,039 | 12/1977 | Nishimura | 357/41 |
| 4,065,782 | 12/1977 | Gray | 357/23 |

*Primary Examiner*—Edward J. Wojciechowicz
*Attorney, Agent, or Firm*—Arthur A. Smith, Jr.; Robert Shaw

[57] ABSTRACT

A charge-flow transistor having a source region and a drain region in a semiconductor substrate, a gate insulator, and a gapped gate electrode with a thin-film material having some electrical conductance disposed in the gap thereof. Metallization patterns are provided to reduce the detrimental effect of parasitic currents that appear within the transistor. There is disclosed also a plurality of such transistors in a single die with metallization to reduce any effect of parasitic currents between the transistors of the plurality.

45 Claims, 12 Drawing Figures

CHARGE-FLOW TRANSISTORS HAVING METALLIZATION PATTERNS

The Government has rights in this invention pursuant to Contract N00014-77-C-0361 awarded by the Department of the Navy.

The present invention relates to charge-flow transistors.

Attention is called to an application for Letters Patent Ser. No. 790,631, filed Apr. 25, 1977, by the present inventor, which application is hereby incorporated herein by reference; said application goes into exhaustive detail in describing charge-flow transistors; such transistors, among other things, have a gapped gate electrode with a thin-film material in the gap. The application, as well as the prior art therein cited, may be used by way of background.

The charge-flow transistors herein described have three principal uses:

First, if the thin-film material disposed in the gap of the transistor's gapped gate electrode has electrical conductance that is sensitive to a property (e.g., the presence of smoke) of the ambient within which the transistor is located, then the transistor serves as a sensor of said property through changes in its electrical characteristics in response to changes in that property.

Second, even if the aforementioned thin-film material has constant electrical conductance, the charge-flow transistor exhibits a turn-on delay that depends on the conductance of said thin-film material; hence, the transistor serves as an extremely compact circuit element for producing time delays, such elements being widely used in digital circuits, computer circuits, timing circuits, and other applications where a specified time interval between two events is required.

Third, the electrical properties of the charge-flow transistor, when compared with corresponding electrical properties of a second identically fabricated transistor differing from the charge-flow transistor only in having a gate electrode with no gap therein, can be used to study the detailed distribution of mobile electric charges within the thin-film material of the charge-flow transistor; such a transistor pair can serve, among other things, to monitor electrical leakage in nominally insulating thin-film materials.

In each of the aforementioned cases, proper use of the charge-flow transistors requires accurate determination of the electrical properties of the transistor. Further work in connection with the transistors described in said application for Letters Patent has shown that parasitic currents appear in the device and have a detrimental effect on the output accuracy of the device. As is discussed in detail, hereinafter, such currents may be found in insulation layers of the transistor as well as in layers provided for passivation.

Accordingly, it is an object of the present invention to provide metallization patterns to reduce any detrimental effect of parasitic currents in charge-flow transistors.

In many uses for charge-flow transistors, it is desired to fabricate a plurality of such transistors, termed an array, on a single piece of semiconductor substrate, termed a die. Parasitic currents have been found to exist between transistors within an array, such as currents, as in the case of the single transistor, having a detrimental effect on the circuit performance of the transistors within the array by causing undesired electrical interaction between the transistors of the array. Accordingly, another object of the present invention is to provide metallization patterns to reduce the detrimental effects of parasitic currents between charge-flow transistors within an array.

The region of the charge-flow transistor that is most sensitive to parasitic currents is the gapped region of the gate electrode within which the thin-film material is disposed. A further object of the present invention is to provide specific metallization means to prevent parasitic currents from entering said gapped region.

In many circuit applications for charge-flow transistor arrays, some of the interconnection between transistors can be accomplished by metallization patterns on the die. Efficient use of space on the die is enhanced when said interconnection can be combined in function with metallization provided to reduce the detrimental effects of parasitic currents. Accordingly, a further object is to combine metallization means to reduce the detrimental effect of parasitic currents with metallization means to accomplish interconnection between transistors of an array of charge-flow transistors.

These and still further objects are addressed hereinafter.

The foregoing objects are achieved, generally, in a charge-flow transistor comprising a semiconductor substrate, a source region, a drain region, a gate insulator, and a gapped gate electrode comprising a pair of fingers with a gap between the fingers. A thin-film material having some electrical conductance is disposed in the gap. A plurality of contacts is provided for making electrical contact respectively to the source region and the drain region. The contacts are insulated from the substrate, from each other and from the gate electrode. The insulation medium, however, is not perfect; hence parasitic electric currents flow in an operating transistor from the contacts and the gate electrode to the substrate, between the contacts and between the contacts and the gate electrode. Such parasitic currents have a detrimental effect on operation of the transistor. Metallization is provided to reduce any such detrimental effect.

The invention is hereinafter described with reference to the accompanying drawing in which.

In order to establish a basis for the explanation later herein, there is first described a charge-flow transistor 100A in FIG. 3, embodying the teachings of the present invention. The transistor 100A is formed on a die 25B and has a substrate 1, a source region 2, a drain region 3, a gate insulator 4, and a gapped gate electrode 5 comprising fingers 5A and 5B with a gap 6 between the fingers (throughout this specification, an attempt is made to apply the same or similar labels to the various elements that provide the same or similar functions). A thin-film material 7 having some electrical conductance, as hereinafter discussed in some detail, is disposed in the gap 6. A contact 9 makes electrical contact at 9A to the source region 2; similarly, a drain contact 10 makes electrical contact at 10A to the drain region 3. Contact pads 9B, 10B and 5C afford electrical connection between outside circuitry and the source region 2, the drain region 3 and the gate 5, respectively: in the explanation below the label 9 and variations thereof are used to designate connection to the source or source region; 10 and variations thereof are used to designate connections to the drain or drain region; and 5 and variations thereof are used to designate the gate connection or gate electrode.

Figure 3:
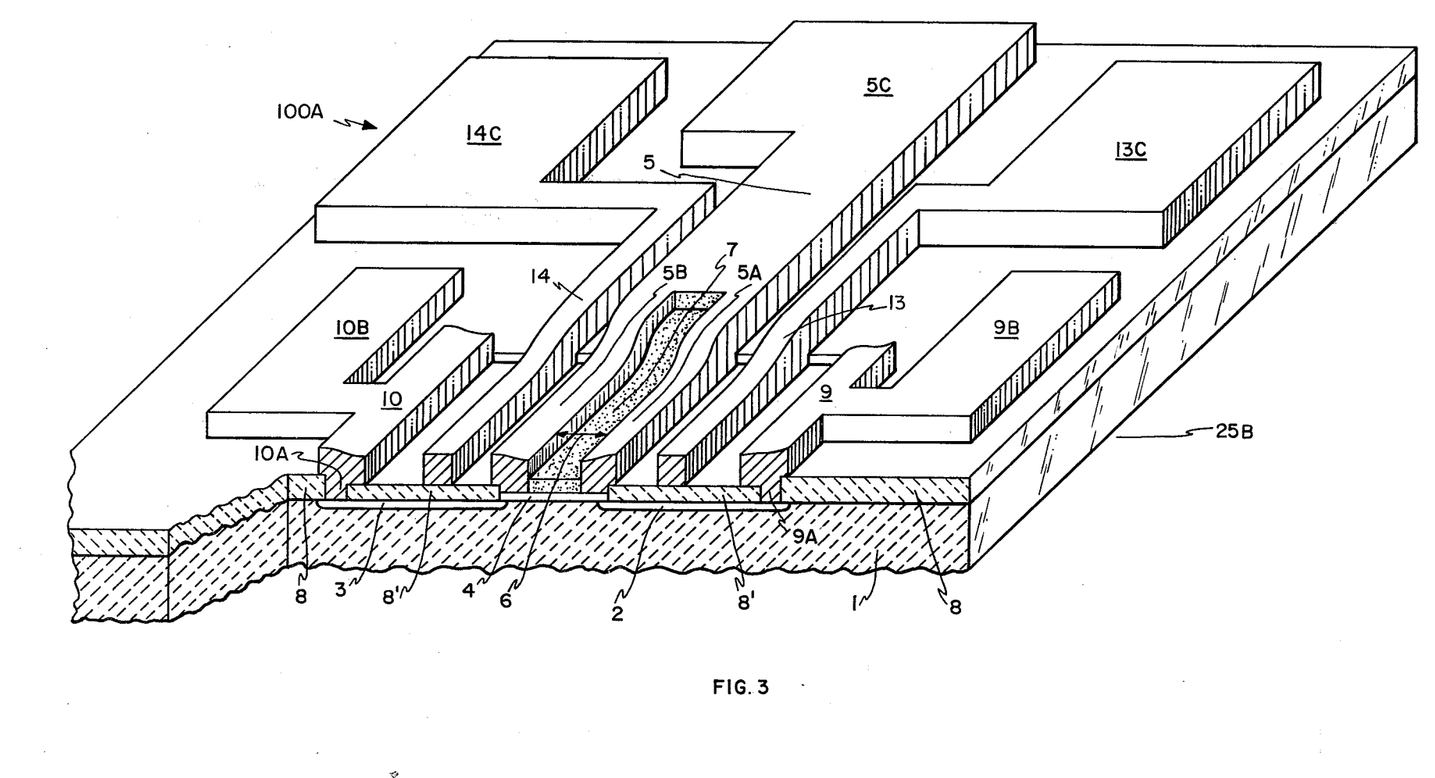
FIG. 3 is an isometric partial view, on an enlarged scale, partly cutaway and partly diagrammatic in form, showing a charge-flow transistor embodying guard bands for the source region and the drain region thereof, disposed so as to reduce the deleterious effects of the parasitic currents of FIG. 1.

Insulating layers 8 and 8' in FIG. 3 serve to insulate the contacts 9 and 10 and the gate electrode 5 from the substrate 1 and from each other. As noted above, the insulating layers 8 and 8' are not perfect, and, hence, parasitic currents can flow between the source and drain contacts, between the contacts and the gate electrode, and from all three to the substrate 1. Further, there is later described with reference to FIG. 5, a passivating layer applied to a device 100E like the device 100A, and parasitic currents also arise by virtue of that passivating layer. It is to mitigate the effect of the parasitic currents that this invention is directed, and toward that end there are provided passive metallization patterns in the form of guard bands such as the guard bands labeled 13 and 14 (with contact pads 13C and 14C, respectively) in FIG. 3 between the gate electrode 5 and the source contact 9 and between the gate electrode 5 and the drain contact 10, respectively. (It will be appreciated at this juncture, that the guard bands 13 and 14 provide guarding as to the pads 9B and 10B as well as to the other portions of the contacts 9 and 10). Passive metallization patterns are also used to reduce the detrimental effect of parasitic currents between transistors of an array of transistors; the term isolation band is employed to designate these metallization patterns, merely to distinguish the same from the guard bands, even though the functions performed are the same. The term "passive" is used to connote that the metallization or conductive means does not operate to control the usual current flow between the source and the drain regions.

Figure 1:
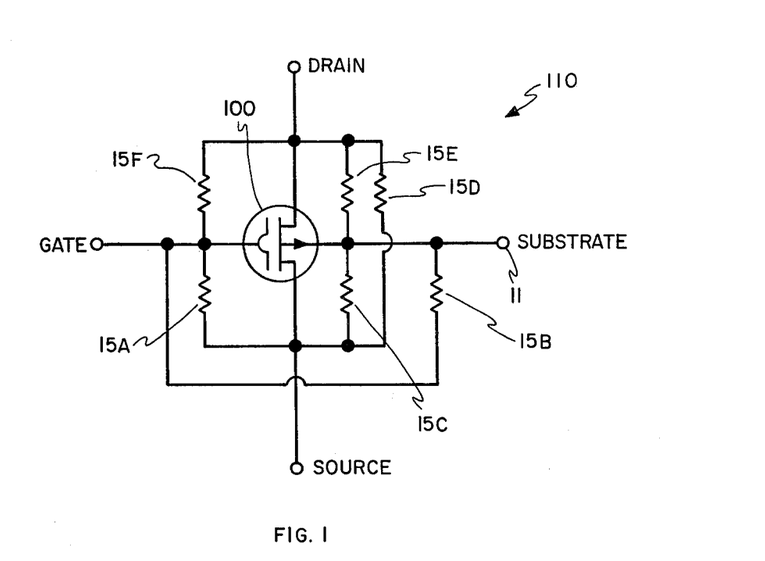
FIG. 1 is an equivalent circuit illustrating schematically the various paths for parasitic current that can exist in a charge-flow transistor.
Figure 2:
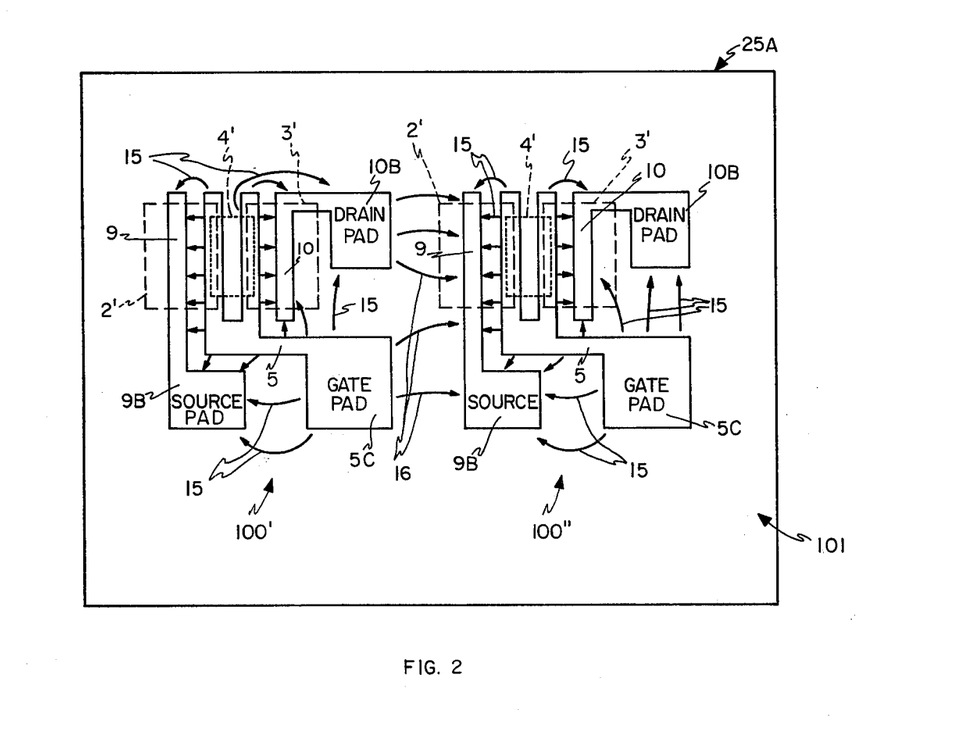
FIG. 2 is the top view of an array of two charge-flow transistors illustrating, in addition, paths for parasitic currents that can exist between transistors of such an array.
Figure 5:
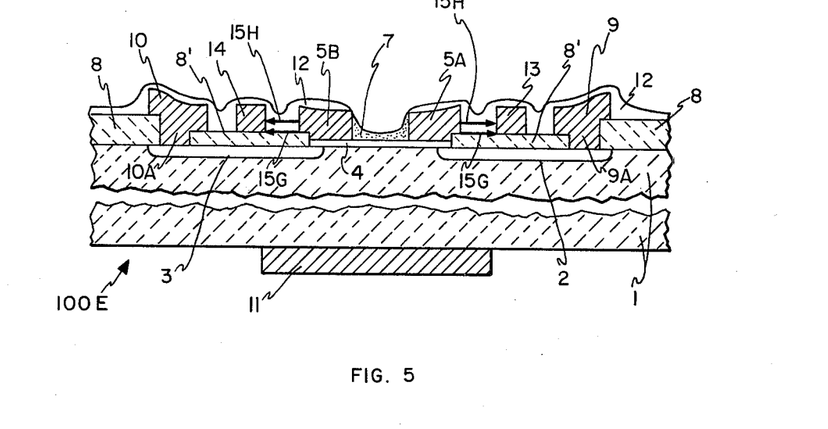
FIG. 5 is a partial section view, on an enlarged scale, of a charge-flow transistor that is a further modification of the device of FIG. 3, showing in more detail the paths for some of the parasitic currents and showing the beneficial effect of the guard bands.

Turning now to FIG. 2, there is shown in schematic top view an array 101 of two charge-flow transistors 100' and 100", which may be like the transistor 100A in FIG. 3 or like the transistor 100E in FIG. 5, fabricated on a single die 25A, except without the guard bands and/or isolation bands of the present invention. The various elements of the transistor 101' and 101" are given identical labels, which labels correspond to those in FIG. 3 and other figures herein. FIG. 2 is included to permit a detailed explanation of parasitic currents; FIG. 1 serves the same purpose; and FIG. 5, to some extent, is similarly used.

Shown in solid outline form in FIG. 2 are the gate electrode 5, the source contact 9, and the drain contact 10 of each of said transistors 100' and 100". Also shown but in broken outline, are the boundaries labeled 2', 3', and 4' of the source region 2, the drain region 3, and the gate insulator 4, respectively, of each of said transistors. The transistors 100' and 100" have parasitic current paths, shown schematically as arrows and labeled 15 in FIG. 2, which paths allow parasitic currents to flow between the source, drain and gate of each transistor in directions substantially parallel to the plane of the substrate.

Referring now to FIG. 1, there is shown an equivalent circuit 110 that comprises a charge-flow transistor 100, like either of the transistors 100' and 100" of the array 101 of FIG. 2, together with resistors 15A, 15D, and 15F connected between the gate, the source and the drain. The three resistors, in combination, represent the electrical effect of the parasitic current paths 15 of FIG. 2. The equivalent circuit 110 also shows resistors 15B, 15C, and 15E that represent the electrical effect of additional parasitic current paths, not shown in FIG. 2, that exist from each of the source, the drain and the gate to a substrate contact 11, the substrate contact 11 being located on the bottom of the die (see the explanation below with reference to FIG. 5) and said parasitic currents flowing in the top surface of the die and over the edge of the die to the substrate contact 11.

Also shown in FIG. 2 are parasitic current paths, illustrated schematically as arrows and labeled 16; the paths 16 allow parasitic current to flow between the transistors 100' and 100". It is the purpose of the present invention, as above indicated, to reduce the detrimental effects of the parasitic currents 15 and 16 on the operation of charge-flow transistors by providing metallization patterns which serve to conduct the parasitic currents away from the sensitive parts of the circuits employing such transistors, as now explained with reference first to FIG. 3 and then FIG. 5.

The insulating layers 8 and 8' in FIG. 3 that serve to insulate the contacts 9, 10, and the electrode 5 from the substrate 1 and from each other, as noted above, are not perfect, and thus, the parasitic currents 15 in FIG. 2 can flow between the electrodes. The guard bands 13 and 14 between the gate electrode 5 and the source contact 9 and between the gate electrode 5 and the drain contact 10, respectively, serve to intercept these parasitic currents 15 of FIG. 2, as is shown in greater detail in FIG. 5 and now discussed.

The charge-flow transistor 100E in FIG. 5 is like the transistor 100A, as indicated above, but it is modified in two ways: First, the substrate contact 11 is provided at the bottom of the substrate, and, second, a passivation layer 12 covers the surface of the device except over the gap region filled with the thin-film material 7. Such passivation layers are used to prevent contamination from reaching the surface of the transistor. It is very convenient, when fabricating charge-flow transistors, to cover the entire device with said thin-film material 7. Hence, in charge-flow transistors, the passivation layer 12 can include a layer of the same thin-film material 7 that is disposed between the fingers 5A and 5B. The electrical conductance of that thin-film material expressed as a sheet conductance is typically greater than that about $10^{-17}$ (ohms/square)$^{-1}$ with an upper limit of electrical conductance at about $10^{-6}$ (ohms/square)$^{-1}$. Some of the parasitic current paths are illustrated in FIG. 5. The paths designated 15G represent current paths from the gate electrode fingers 5A and 5B along the upper surface of the insulator 8' or the lower surface of passivation layer 12, while the paths designated 15H represent current paths from gate electrode fingers 5A and 5B entirely within the passivation layer 12. The guard bands 13 and 14 in FIG. 5 intercept both of the current paths 15G and 15H and, hence, prevent parasitic currents in these paths from reaching the source contact 9 and the drain contact 10.

Figure 4:
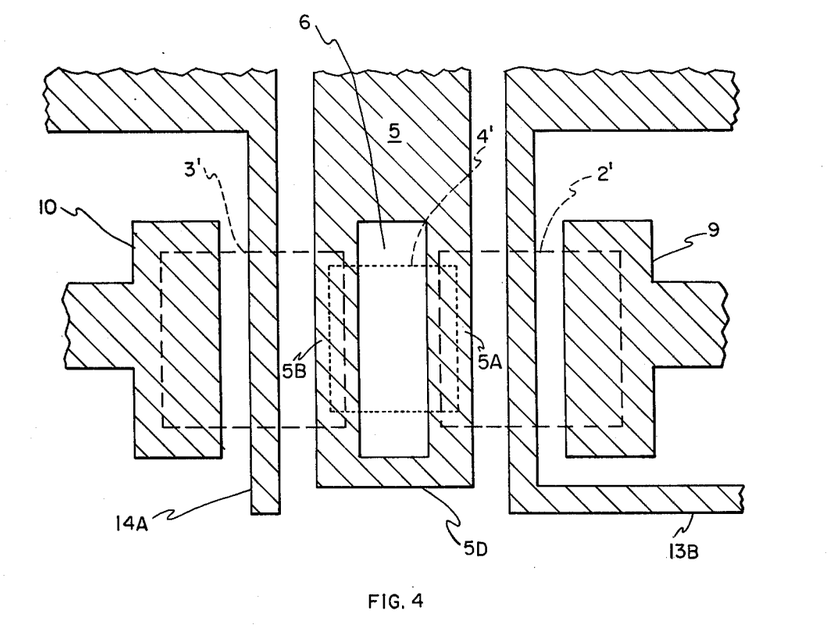
FIG. 4 is a detailed partial top view on an enlarged scale, partly diagrammatic in form, of a modification of the transistor of FIG. 3, showing parts of the guard bands and, schematically, outlines of the source region, the drain region, and a gate insulator of the transistor.

Turning now to FIG. 4, there is shown an enlarged partial top view of a charge-flow transistor metallization pattern. Again, shown in broken outline form are the boundaries 2', 3', and 4' of the source region, the drain region, and the gate insulator, respectively. Disposed between the drain contact 10 and the gate electrode 5 is a guard band 14A, like 14 of FIGS. 3 and 5. Also shown disposed about the source contact 9 is a guard band 13B, like the guard band 13 of FIGS. 3 and 5, but providing complete enclosure of the source contact, as shown further at 13B of FIGS. 6 and 7. Returning to FIG. 4, there is also shown gap closure metallization 5D that connects the far ends of the fingers 5A and 5B, thereby completely surrounding gap region 6 and preventing any parasitic currents from flowing in the electrically sensitive region above the gate insulator, bounded by 4'. While guard bands such as 13B and 14B of FIG. 6 prevent parasitic currents from reaching the source contact 9 and the drain contact 10, respectively, and while the gap closure metallization 5D of FIGS. 4 and 7 prevents parasitic currents from reaching the gate gap 6, there remain the possible parasitic paths 16 of FIG. 2 between the transistors of an array and also the parasitic paths from the source, drain and gate (as represented respectively by the resistors 15C, 15E and 15B in FIG. 1) to the substrate contact 11.

Figure 6:
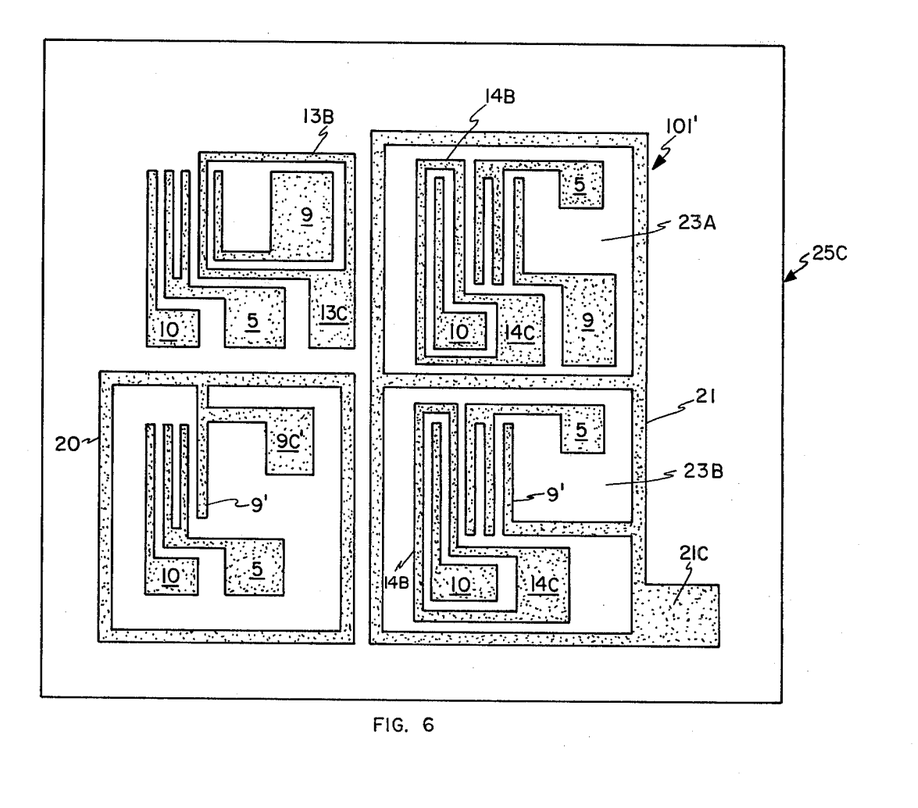
FIG. 6 is a top view showing metallization patterns, in outline form, of an array of charge-flow transistors, embodying modifications of the guard bands of FIG. 3 and, also, isolation bands disposed so as to reduce the deleterious effects of the parasitic currents between transistors of an array like the array of FIG. 2.

FIG. 6 shows an array 101' disposed on a die 25C and comprising four charge-flow transistors. One transistor has a guard band, again marked 13B, surrounding the source contact 9 thereof and having contact pad, again marked 13C. The guard band 13B in FIG. 6 forms a closed loop about the source contact 9, as shown, to achieve isolation of that source contact 9 from the drain contact and the gate electrode of the transistor, but also from a substrate contact (if the array 101' has such contact) and from the other transistos of the array 101'. The remaining three transistors of the array are surrounded by isolation bands to prevent parasitic currents from flowing between transistors, as described in detail in what now follows.

The isolation band marked 20 in FIG. 6 is disposed about a single transistor of the array and is connected to the source contact marked 9' of said single transistor; a contact pad 9C' provides common electrical contact for both isolation band 20 and source contact 9'. An isolation lattice 21, with contact pad 21C, has a transistor disposed in each cell of the lattice comprising the cells labeled 23A and 23B. The transistor inside the cell 23A has a guard band 14B having contact pad 14C disposed about the drain contact 10 thereof. The transistor in the cell 23B differs only in having its source contact 9' connected to the isolation lattice 21. Both the isolation band 20 and the isolation lattice 21 prevent any parasitic currents from flowing between transistors of the array, and they also prevent parasitic currents from flowing over the edge of the die 25C to a substrate contact (if the array 101' has a substrate contact) from the source contact and/or the drain contact and/or the gate electrode of the transistors isolated thereby.

Figure 7:
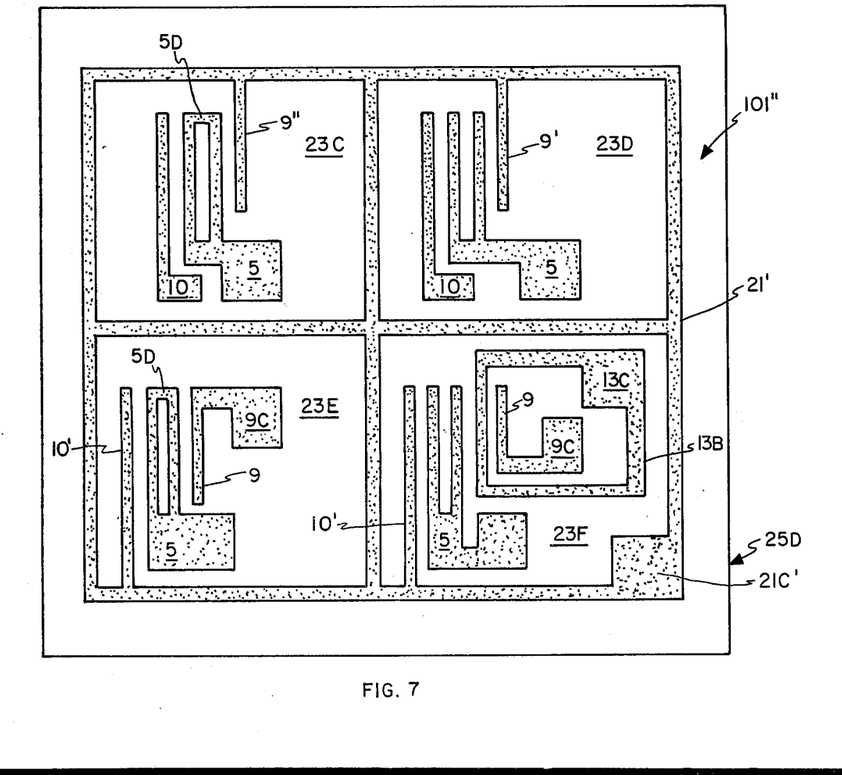
FIG. 7, like FIG. 6, is a top view, in outline form, of further modifications of metallization patterns.

Further metallization patterns are shown in FIG. 7, which illustrates an array 101'' disposed on a die 25D, comprising four charge-flow transistors, each disposed within a cell of an isolation lattice 21' (with a contact pad 21C') comprising cells 23C, 23D, 23E and 23F. The transistor of the array in the cell 23D has its source contact 9' connected to the isolation lattice 21'. The transistor in the cell 23C has a gap closure metallization 5D and its source contact 9'' connected to the isolation lattice 21'. The transistor in the cell 23E has gap closure metallization 5D and a drain contact 10' that is connected to isolation lattice 21'. The transistor in the cell 23F has a guard band 13B (with a contact pad 13C) disposed about the source contact 9 and a drain contact 10' that is connected to the isolation lattice 21'.

Figure 11:
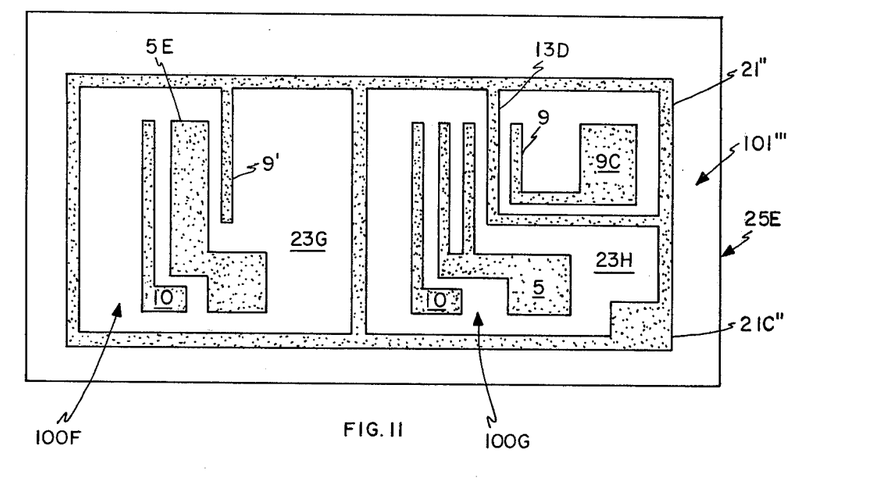
FIG. 11 is a top view of a two-transistor array with metallization patterns.

Still further metallization patterns are shown in FIG. 11, which shows a two-transistor array 101'''' (comprising transistors 100F and 100G) disposed on a die 25E, each transistor disposed within a cell of isolation lattice 21'' comprising cells 23G and 23H. The transistor 100F of the array in the cell 23G has a solid gate electrode 5E and, hence, is a conventional field-effect transistor. Such transistors are used in combination with the charge-flow transistors herein to make integrated circuits, and to make measurements which, when combined with corresponding measurements on a charge-flow transistor, permit monitoring of conduction processes in the thin-film material in the charge-flow transistor as explained below with reference to FIG. 12. Hence, such field-effect transistors must also be isolated from the effects of parasitic currents by a lattice like 21''. The charge-flow transistor 100G has a guard band 13D disposed about its source contact 9 and connected to the isolation lattice 21''. Hence, part of the isolation lattice 21'' also serves to complete the guard band about the source contact 9 or the charge-flow transistor 100G.

Figure 12:
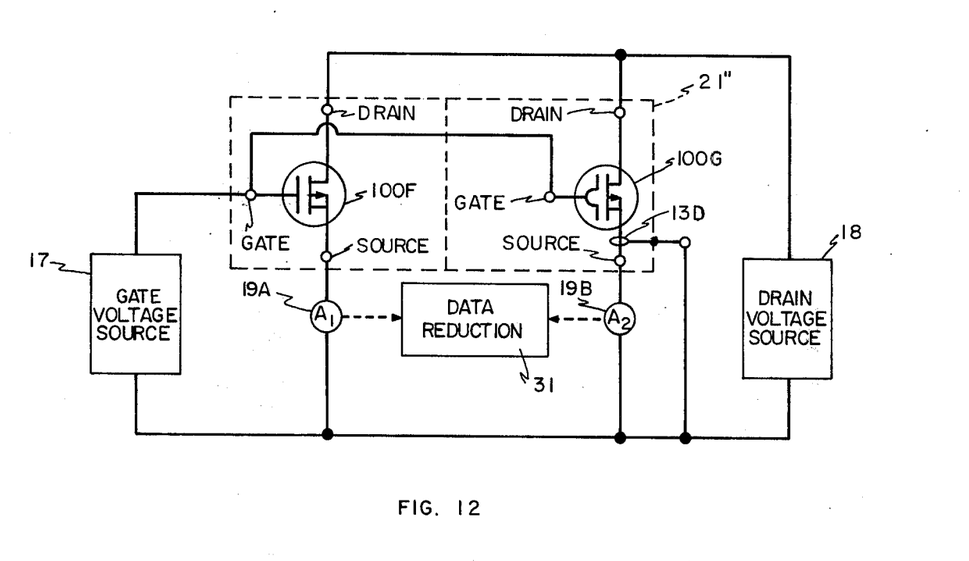
FIG. 12 is a schematic of analyzing circuitry that includes the two transistors of FIG. 11.

In the analyzing circuit of FIG. 12 the transistors 100F and 100G are connected to permit analysis of the conduction processes in the thin-film material in the gapped gate of the charge-flow transistor 100G. The circuit of FIG. 12 includes a gate voltage source 17 to establish a bias voltage between the gate of each of the transistors 100F and 100G and either source thereof; there is further included a drain voltage source to establish a voltage between the drain and source 18 of each of the transistors 100F and 100G. Ammeters 19A and 19B measure either the drain or source current of both of the transistors 100F and 100G to give an output signal as to each transistor. Data reduction means 31 is connected to receive the output signal from each of the ammeters 19A and 19B and is operable to extract from the output signals and from variations therein (due to varying the gate bias) the average distance of mobile charge carriers in the thin-film material (i.e., the thin-film 7 in FIG. 3) of the charge-flow transistor 100G from the interface between the gate insulator (i.e., the insulator 4 in FIG. 3) and the thin-film material.

Figure 8:
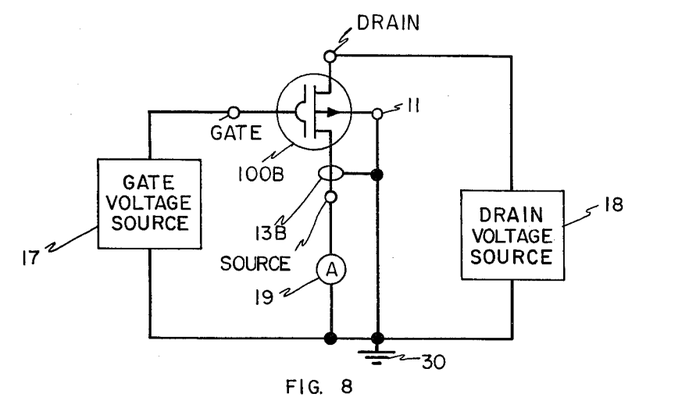
FIG. 8 is a circuit diagram in which the source current of a charge-flow transistor embodying the present inventive concept is measured without interference from parasitic currents.
Figure 9:
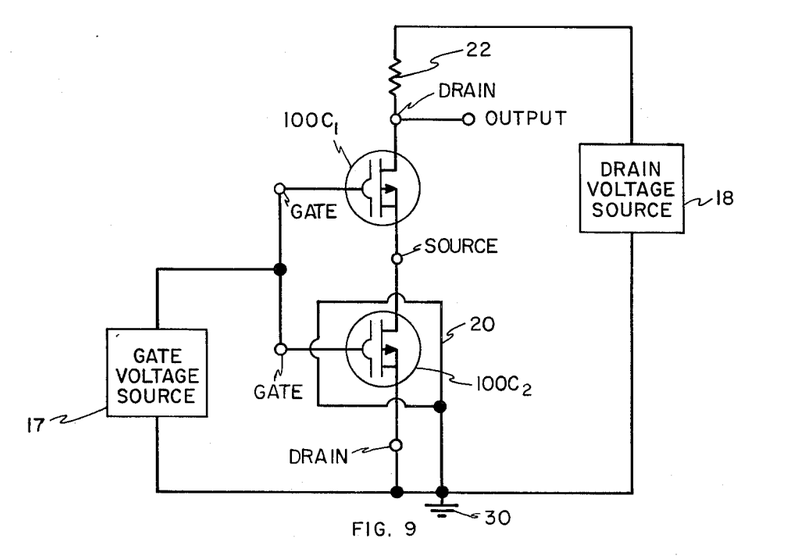
FIG. 9 is a circuit diagram which shows the use of isolation bands to eliminate the effect of parasitic currents between transistors.
Figure 10:
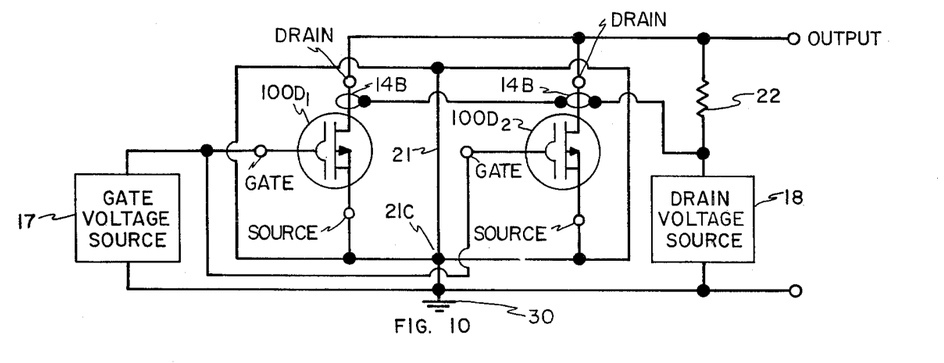
FIG. 10 shows a circuit in which a plurality of transistors embodying both isolation and guard bands is used.

Methods of using guard bands and isolation bands in circuits are illustrated in FIGS. 8, 9, and 10. Turning first to the circuit of FIG. 8, there is shown a charge-flow transistor 100B which has a guard band 13B about the source contact connected to the substrate contact 11. The gate voltage source again designated 17 in FIGS. 8–10 provides a drive signal to the gate and the drain voltage source 18 provides a bias voltage to the drain. Current monitoring means 19 is connected between the source and circuit ground 30. Because of the guard band 13B, all parasitic currents that might flow to the source in FIG. 8 and, hence, through the current monitor 19 are intercepted by the guard band 13B, as previously explained with regard to FIG. 5, and are directed to the circuit ground 30 without passing through the current monitor 19. Thus, the current measured by the current monitor 19 is only the actual source current of the charge-flow transistor 100B, free of interference from parasitic currents. A circuit of this type is used for monitoring the turn-on delay of the charge-flow transistor in applications where the conductivity of the thin-film material 7 of FIG. 5 depends on a parameter of the environment (e.g., the presence of smoke or humidity), and, therefore, the turn-on delay serves as a measure of the environmental parameter to which the thin-film material is sensitive. Parasitic currents interfere directly with the measurement of turn-on delay because they arise in response to an applied gate voltage drive from gate voltage source 17 and from the drain voltage source 18 in a manner which cannot be distinguished from the actual source current. In charge-flow transistors without guard bands in which the thin-film material 7 of FIG. 5 and passivation layer 12 comprises the polymer poly (p-amino phenylacetylene), a humidity-sensitive thin-film material, parasitic currents as large as one microampere have been observed, using the technique of measuring the current at the gate contact, which should be less than $10^{-6}$ microamperes in the absence of parasitic currents. Parasitic currents of this microampere magnitude are comparable to the transistors source current and thus must be intercepted with guard bands.

Turning now to FIG. 9, there is shown a circuit with two charge-flow transistors $100C_1$ and $100C_2$, which transistors have their sources and substrates connected together. The transistors $100C_1$ and $100C_2$ form an array of transistors, and one, the transistor $100C_2$, is surrunded by an isolation band 20. The circuit also contains a gate voltage source 17, a drain voltage source 18, and a load resistor 22. Ideally, in the absence of parasitic currents, when both transistors $100C_1$ and $100C_2$ are off, the output voltage equals the drain voltage source value. Furthermoe, in the absence of parasitic currents, following the application of a gate voltage from the gate voltage source 17, the output voltage drops only after both the transistors $100C_1$ and $100C_2$ have completed their respective turn-on delays. Thus, the circuit of FIG. 9 serves as a logic function, that of selecting the longer of the two turn-on delays. With parasitic currents, two problems arise. First, some of the parasitic current flows through the resistor 22 even with both transistors off. Second, in the absence of the isolation band 20 in FIG. 9, the turn-on of the transistor $100C_1$ modifies the amount of parasitic current reaching the transistor $100C_2$ from the transistor $1001C_1$, thus causing a change in output voltage before both transistors have turned on. The isolation band 20 prevents the distribution of parasitic currents (like the currents 16 of FIG. 2) between transistors from affecting the circuit output. Improved performance in this regard would be obtained with both transistors isolated, as shown in FIG. 10 and now explained.

Transistors $100D_1$ and $100D_2$ in FIG. 10 are part of an array; each is disposed within a cell of isolation lattice 21, said lattice being also connected at 21C to circuit ground 30 and to the source of each transistor (as shown in FIG. 6, wherein one of the transistors has its source contact 9' connected to the isolation lattice 21). This circuit, like that of FIG. 9, performs a logic function, in this case the selection of the shorter of two turn-on delay times. The transistors $100D_1$ and $100D_2$ have guard bands 14B disposed about the drain contacts, said guard bands being connected to drain voltage source 18. The isolation lattice 21 in FIG. 10 prevents any interaction between the transistors $101D_1$ and $101D_2$ while the drain guard bands 14B conduct parasitic currents within each transistor away from load resistor 22, thereby preventing said parasitic currents from affecting the circuit output.

A few comments of a general nature are contained in this paragraph and the next. The guard bands and the isolation bands described above act to prevent parasitic currents which would otherwise give spurious indication in circuits like FIGS. 8–10, for example, from introducing such spurious indications; this is a very important consideration in devices of the type described in said application for Letters Patent because the signals in such devices are so very small and are amplified so greatly that any spurious signals can render the devices inoperative. The metallization patterns herein disclosed reduce the effects of the parasitic currents to acceptable levels. It will be appreciated on the basis of the foregoing explanation that the guard bands may be guard rings (i.e., closed loop) as shown at 13B and 14B in the figures, but such is not always necessary (see, for example, the guard bands 13 and 14 in FIG. 3 and 14A in FIG. 4). Also, whether the isolation bands are closed loop metallization of the type disclosed in FIGS. 6 and 7, for example, or strips (i.e., a portion only of the closed-loop bands of FIGS. 6 and 7) will depend on the stringencies of the apparatus within which the devices are used. In any circumstance, the extent to which a metallization pattern surrounds and isolates an active transistor element must be sufficient to fit the requirements of that particular transistor. Also, it will be noted that both the source and drain contacts, the gate electrode and the various metallizations are all disposed at the one major surface of the transistor; the necessary metallization can be applied by evaporation or other techniques described in the patent application above mentioned.

In general the various devices described herein can be fabricated by the MOS fabrication techniques discussed in said patent application. Some dimensions of importance are as follows: the width of the gap 6 is ~0.1 to 1.5 mils, the length of the fingers 5A and 5B is typically ~10 mils, the thickness of the thin film 7 (which may be a polymer as described in said patent application) is about 3000A.

Further modifications of the present invention will occur to persons skilled in the art and all such modifications are deemed to be within the scope of the invention as defined by the appended claims.

What is claimed is:

1. A charge-flow transistor comprising: a semiconductor substrate; a source region; a drain region; a gate insulator; a gapped gate electrode comprising a pair of fingers with a gap between the fingers; a material having some electrical conductance disposed in said gap; contacting means comprising a plurality of contacts for making electrical contact to the source region and the drain region; insulating means to insulate said contacts from the substrate, from each other and from the gate electrode and the gate electrode from the substrate, said insulating means being imperfect and thus permitting parasitic currents to flow in directions substantially parallel to the plane of said substrate between said contacts and between said contacts and the gate electrode; and passive metallization means positioned on said transistor to intercept and conduct away said parasitic currents.

2. A charge-flow transistor as claimed in claim 1 in which said insulating means comprises a layer of insulating material disposed between said substrate and said contacts and the gate electrode, and in which at least some of said parasitic currents are currents that pass along the surface of said insulating layer to which said contacts and said gate electrode are affixed.

3. A charge-flow transistor as claimed in claim 1 in which said insulating means comprises, in combination, a layer of insulating material disposed between said substrate and said contacts and a passivating layer disposed over the surface of said insulating layer and in which at least some of said parasitic currents are currents that pass through said passivating layer.

4. A charge-flow transistor as claimed in claim 3 in which at least some of the passivating layer is formed of the same material as the material in said gap.

5. A transistor array that comprises a plurality of the charge-flow transistors of claim 1 on a single die and in which said metallization means is appropriately disposed to isolate one transistor from another as regards said parasitic currents.

6. A transistor array as claimed in claim 5 in which the metallization means comprises a metallized lattice and in which at least some of the transistors of said plurality are disposed within individual cells of the lattice.

7. A transistor array is claimed in claim 5 in which the metallization means comprises a metallized lattice and in which each transistor of said plurality is disposed within a cell of the lattice.

8. A transistor array as claimed in claim 5 in which the metallization means comprises an isolation band around at least one transistor of the plurality.

9. A transistor array as claimed in claim 8 wherein at least one of said transistors has its source contact in common with said isolation band.

10. A transistor array as claimed in claim 8 wherein at least one of said transistors has its drain contact in common with said isolation band.

11. A transistor array as claimed in claim 8 whrein at least one of the transistors of the array has a guard band disposed between at least one of the source contact and the drain contact and the gate electrode thereof.

12. A transistor array as claimed in claim 11 wherein at least one of the source contact and the drain contact is in common with said isolation band.

13. A transistor array as claimed in claim 12 wherein a substrate contact is provided to permit direct electrical connection to the substrate.

14. A charge-flow transistor as claimed in claim 1 wherein the electrical conductance of said material in said gap is greater than about $10^{-17}$ (ohms/square)$^{-1}$.

15. A charge-flow transistor as claimed in claim 14 in which the upper limit of said electrical conductance is no greater than about $10^{-6}$(ohms/square)$^{-1}$.

16. A charge-flow transistor as claimed in claim 1 wherein the contact of said plurality, the gapped gate electrode and the metallization means are all thin metal layers disposed at one major surface of the transistor and in which the metallization means comprises a guard band at said one major surface and positioned between one of the contacts of said plurality and at least one of the gate electrode and naother contact of said plurality.

17. An array of transistors formed on a single die and comprising a plurality of charge-flow transistors as claimed in claim 1, said metallization means comprising an isolation band disposed between one transistor of the array and any other transistor of the array.

18. An array of transistors as claimed in claim 17 in which the isolation band is in the form of a closed-loop metallization disposed at one major surface of the die and surrounding the source contact, the drain contact and the gate electrode of said one transistor at said one major surface.

19. An array of transistors as claimed in claim 18 in which said metallization further includes a guard band disposed at said one major surface and positioned between one of the contacts of said plurality and at least one of the gate electrode and another contact of said plurality.

20. An array of transistors formed on a single die that comprises a charge-flow transistor as claimed in claim 1 and including a conventional field effect transistor comprising: a source region, a drain region, a gate insulator, a gate electrode, contacting means comprising a plurality of contacts for making electrical contact to the source region and the drain region of the conventional field effect transistor, and insulating means to insulate the contacts of the conventional field effect transistor from the semiconductor substrate, from each other and from the gate electrode of the conventional field effect transistor from the semiconductor substrate.

21. An electric circuit comprising an array of transistors as claimed in claim 20 and further including gate bias means to establish a bias voltage between the gate of each transistor and either the source or drain thereof; drain bias means to establish a voltage between the drain and source of each transistor of the array; means to measure either the source or drain current of both transistors of the array and to give an output signal for each transistor; and data reduction means operable to extract from said output signal and from variations therein due to varying the gate bias the average distance of the mobile charge in the material in said gap from the interface between the gate insulator and said material.

22. An array of transistors formed on a single die that comprises a charge-flow transistor as claimed in claim 1 and including a conventional field effect transistor comprisng: a source region, a drain region, a gate insulator, a gate electrode, contacting means comprising a plurality of contacts for making electrical contact to the source region and the drain region of the conventional field effect transistor, insulating means to insulate the contacts of the conventional field effect transistor from the semiconductor substrate, from each other and from the gate electrode of the conventional field effect transistor and the gate electrode of the conventional field effect transistor from the semiconductor substrate, the insulating means of the conventional field effect transistor being imperfect and thus permitting parasitic currents to flow between the contacts and gate electrode thereof and between the contacts and gate electrode thereof and the semiconductor substrate; and metallization means to reduce any detrimental effect on use of the conventional field effect transistor due to parasitic currents therein.

23. A charge-flow transistor that comprises: a semiconductor substrate; a source region; a drain region; a gate insulator; a gapped gate electrode; a material disposed in the gap of the gapped gate electrode; contacting means making electrical contact respectively to the source region and the drain region; insulating means that insulates the contacting means of the source region and the drain region from the substrate, from each other and from the gate electrode, which insulating means is not perfect so that parasitic currents flow between elements of the transistor in directions substantially parallel to the plane of said substrate; and passive metallization means positioned on said transistor to intercept and conduct away said parasitic currents.

24. A charge-flow transistor comprising: a semiconductor substrate; a source region; a drain region; gapped gate electrode means comprising a pair of conductive fingers with a gap between the fingers; a material having some electrical conductance disposed in said gap and in electrical contact with the conductive fingers, the conductance of said material being much less than the conductance of said conductive fingers; a gate insulator interposed between the pair of conductive fingers and said substrate, said fingers and said material being disposed in the electrically sensitive region immediately adjacent to the gate insulator; contacting means comprising a plurality of contacts for making electrical contact to the source region and the drain region; insulating means to insulate said contacts from the substrate, from each other and from the gate electrode means and the gate electrode means from the substrate, said insulating means being imperfect and thus permitting parasitic currents to flow in directions substantially parallel to the plane of said substrate between said contacts and between said contacts and the gate electrode means; and passive conductive means positioned on said transistor to intercept and conduct away said parasitic currents.

25. A charge-flow transistor as claimed in claim 24 where in said conductive means comprises metallization patterns disposed at the surface of the transistor to intercept parasitic currents flowing in the surface of the charge-flow transistor.

26. Apparatus as claimed in claim 24 having gap closure metallization at the ends of said fingers completely surrounding the gap region to prevent parasitic currents from flowing in said electrically sensitive region about the gap insulator.

27. Apparatus as claimed in claim 24 wherein the gapped gate electrode means, the material in said gap and the plurality of contacts are all at one major surface of the charge-flow transistor and constitute at least some of the active elements of the charge-flow transistor, said conductive means comprising metallization patterns positioned to isolate said active elements against parasitic currents therebetween.

28. Apparatus as claimed in claim 24 wherein the material in the gap is a thin-film material and has an electrical conductance, expressed in sheet conductance, that is greater than about $10^{-17}$ (ohms/square)$^{-1}$ with an upper limit at about $10^{-6}$ (ohms/square)$^{-1}$.

29. Apparatus as claimed in claim 24 in which the gate insulator is an insulator region formed on said substrate bridging the substrate region between the source region and the drain region, said conductive fingers being connected together at one end of each finger, said conductive fingers extending across and beyond said electrically sensitive region, the connection between the fingers being outside the electrically sensitive region.

30. Apparatus as claimed in claim 29 having a gap closure conductor at both ends of said fingers to provide conductive means that completely surrounds the gap region to prevent parasitic currents from flowing in said electrically sensitive region, the gap closure conductor at both ends being outside the electrically sensitive region.

31. A charge-flow transistor as claimed in claim 1 wherein said contacts and the gapped gate electrode comprise metallizations at one major surface of the charge-flow transistor.

32. Apparatus as claimed in claim 31 wherein the conductance of said material in said gap, expressed as a sheet conductance, is greater than about $10^{-17}$ (ohms/square)$^{-1}$ with an upper limit of electrical conductance at about $10^{-6}$ (ohms/square)$^{-1}$.

33. A charge-flow transistor comprising: a semiconductor substrate; a source region; a drain region; gapped gate electrode means comprising a pair of conductive fingers with a gap between the fingers; a gap material having some electrical conductance disposed in said gap and in electrical contact with the conductive fingers, the conductance of the gap material being much less than the conductance of said conductive fingers; a gate insulator interposed between the pair of conductive fingers and said substrate and between the gap material and the substrate, said fingers and said gap material being disposed in the electrically sensitive region immediately adjacent to the gate insulator; contacting means comprising a plurality of contacts for making electrical contact to the source region and the drain region; insulating means to insulate said contacts from the substrate, from each other and from the gate electrode means and the gate electrode means from the substrate, said insulating means being imperfect and thus permitting parasitic currents to flow in directions substantially parallel to the plane of said substrate between said contacts and between said contacts and the gate electrode means; and passive conductive means positioned on said transistor to intercept and conduct away said parasitic currents.

34. A charge-flow transistor as claimed in claim 33 in which the metallization means comprises a guard band disposed between the source contact and the gate electrode.

35. A charge-flow transistor as claimed in claim 34 having a contact pad electrically connected to said guard band.

36. A charge-flow transistor as claimed in claim 33 in which the metallization means comprises a guard band disposed about the source contact.

37. A charge-flow transistor as claimed in claim 36 having a contact pad electrically connected to said guard band.

38. A charge-flow transistor as claimed in claim 33 in which the metallization means comprises a guard band disposed between the drain contact and the gate electrode.

39. A charge-flow transistor as claimed in claim 38 having a contact pad electrically connected to said guard band.

40. A charge-flow transistor as claimed in claim 33 in which the metallization means comprises a guard band disposed about the drain contact.

41. A charge-flow transistor as claimed in claim 40 having a contact pad electrically connected to said guard band.

42. A charge-flow transistor as claimed in claim 33 in which the fingers of the gate electrode are connected to one another by metallization at both ends of the gap.

43. A charge-flow transistor as claimed in claim 33 in which the metallization means comprises a guard band disposed between one of the contacts of said plurality and at least one of the gate electrode and another contact of said plurality.

44. A charge-flow transistor as claimed in claim 43 in which the guard band is a closed-loop metallization that surrounds said one of the contacts.

45. A charge-flow transistor as claimed in claim 33 wherein the material in said gap is thin-film material with thickness of the order of 3000A.

* * * * *